US00PP30264P2

(12) United States Plant Patent
Benetka

(10) Patent No.: US PP30,264 P2
(45) Date of Patent: Mar. 5, 2019

(54) ***WEIGELA* PLANT NAMED 'VUKOZ047213'**

(50) Latin Name: *Weigela hybrida*
Varietal Denomination: VUKOZ047213

(71) Applicant: Vojtech Benetka, Chodov (CZ)

(72) Inventor: Vojtech Benetka, Chodov (CZ)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 15/732,448

(22) Filed: Nov. 15, 2017

(51) Int. Cl.
*A01H 5/02* (2018.01)

(52) U.S. Cl.
USPC ..... Plt./226

(58) Field of Classification Search
USPC ..... Plt./226
See application file for complete search history.

*Primary Examiner* — Keith O. Robinson
(74) *Attorney, Agent, or Firm* — Cassandra Bright

(57) ABSTRACT

A new and distinct *Weigela* plant named 'VUKOZ047213' is disclosed, characterized by rich flowering and re-blooming of light pink flowers. Foliage is distinctively green with yellow-green flushing. Plants are low growing. The new variety is a *Weigela*, normally produced as an outdoor garden plant.

2 Drawing Sheets

Latin name of the genus and species: *Weigela hybrida.*
Variety denomination: 'VUKOZ047213'.

BACKGROUND OF THE INVENTION

The new *Weigela* cultivar is a product of a planned breeding program conducted by the inventor, Vojtech Benetka, in Pruhonice, Czech Republic. The objective of the breeding program was to produce new *Weigela* varieties with white flowers. The cross resulting in this new variety was made in 2004.

The seed parent is an unpatented, unnamed proprietary *Weigela* referred to as '00-1-20'. The pollen parent is the unpatented, *Weigela* 'Dark Horse'. The new variety was identified as a potentially interesting selection in 2010, at a research nursery in Pruhonice, Czech Republic.

Asexual reproduction of the new cultivar 'VUKOZ047213' by softwood cuttings was first performed in 2010, at a research nursery in Pruhonice, Czech Republic. Subsequent propagation has shown that the unique features of this cultivar are stable and reproduced true to type in five successive generations.

SUMMARY OF THE INVENTION

The cultivar 'VUKOZ047213' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'VUKOZ047213'. These characteristics in combination distinguish 'VUKOZ047213' as a new and distinct *Weigela* cultivar:

1. Yellowish-green foliage.
2. Low growth habit.
3. Light pink flowers.
4. Reblooming.
5. Rich flowering.

PARENT COMPARISON

Plants of the new cultivar 'VUKOZ047213' are similar to plants of the seed parent in most horticultural characteristics; however, plants of the new cultivar 'VUKOZ047213' differ in the following:

1. New cultivar has light pink flowers, whereas the parent has darker pink flowers.

Plants of the new cultivar 'VUKOZ047213' are similar to plants of the pollen parent in most horticultural characteristics; however, plants of the new cultivar 'VUKOZ047213' differ in the following:

1. New cultivar has yellowish-green foliage, whereas the parent has dark purple foliage.
2. New cultivar has light pink flowers, whereas parent has crimson flowers.

COMMERCIAL COMPARISON

Plants of the new cultivar 'VUKOZ047213' can be compared to the unpatented commercial variety *Weigela* 'Looymansii Aurea'. These varieties are similar in most horticultural characteristics, however 'VUKOZ047213' differs in the following:

1. New cultivar's leaves are yellow-green, this comparator has green foliage.
2. New cultivar is more compact and dwarf, whereas this comparator variety is lankier and taller.
3. New cultivar has light pink flowers; this comparator's flowers are more purple on outside, and pink on inside.

BRIEF DESCRIPTION OF THE PHOTOGRAPHS

Figure 1:
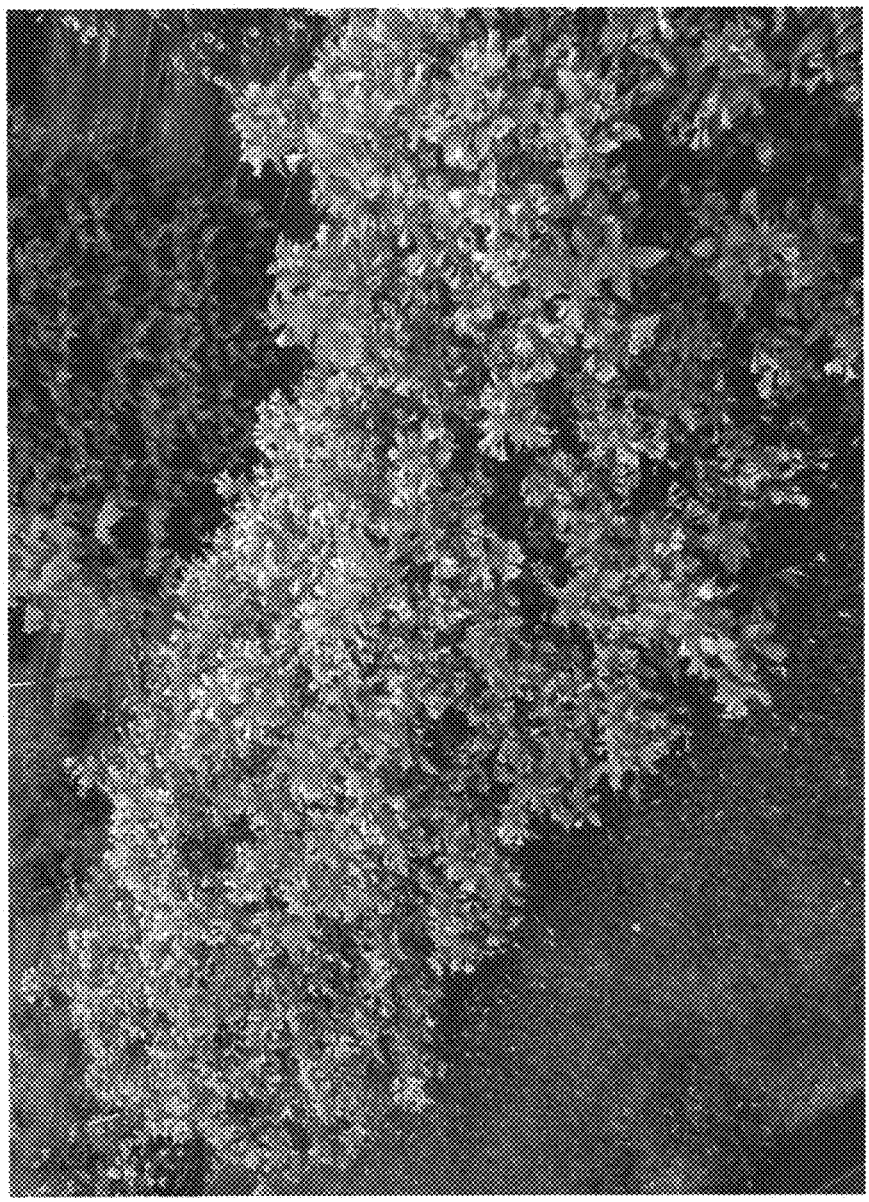

The accompanying photograph in FIG. 1 illustrates in full color a side view perspective of a typical plant of 'VUKOZ047213' grown outdoors.

Figure 2:
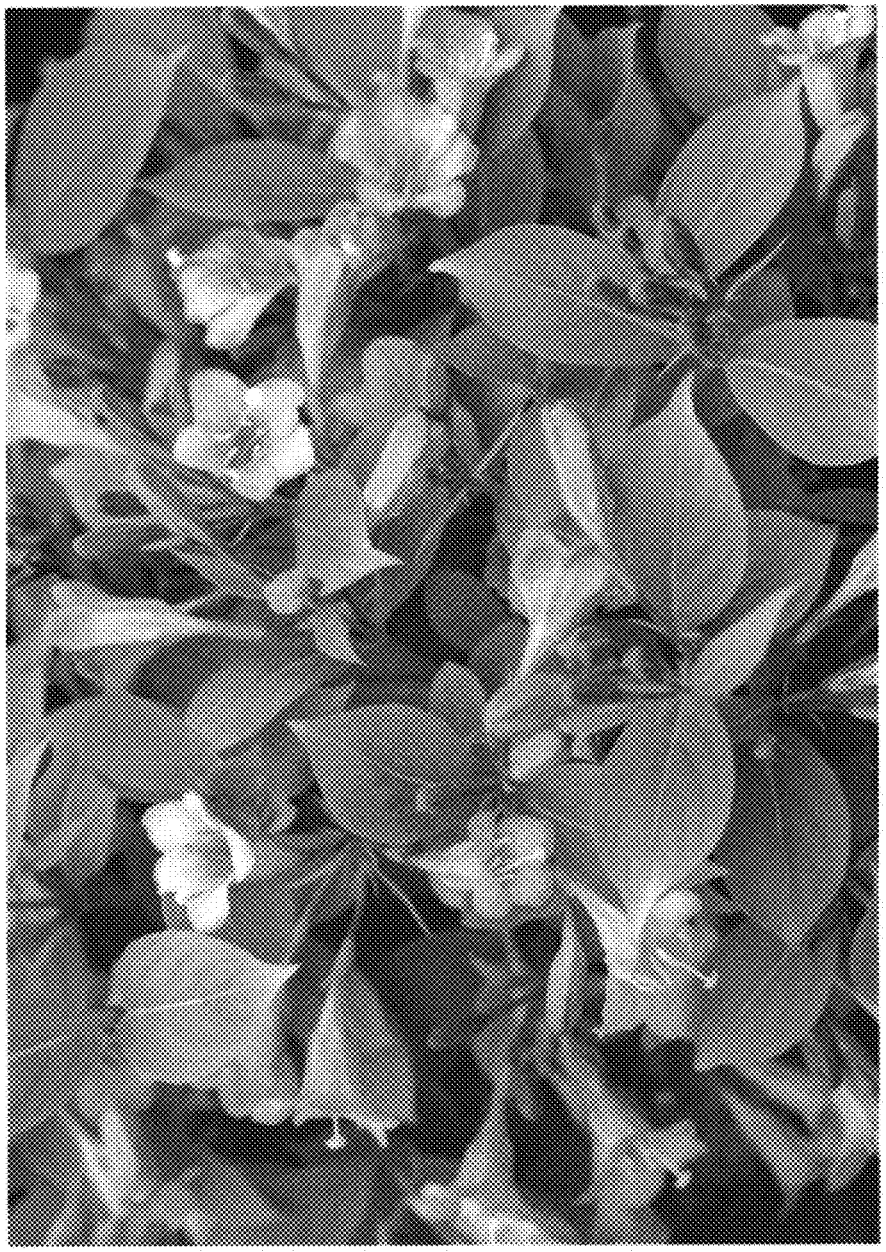

FIG. 2 illustrates the same plant with a close-up view of the flowers and foliage. Age of the plant photographed is approximately 3 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'VUKOZ047213' plants grown in a poly house in Grand Haven, Mich. Measurements were taken during late Spring. The plants were 2 years old. The growing temperature ranged from approximately 5° C. to 27° C. Measurements and numerical values represent averages of typical plant types.

Botanical classification: *Weigela hybrida* 'VUKOZ047213'.

PROPAGATION

Time to initiate roots: Approximately 15 days.

Root description: Density is dense and freely branching. Thin root thickness. White in color, not effectively measured with a color chart.

Time to produce a rooted young plant: Approximately 60 days.

PLANT

Plant type: Shrub.
Age of plant described: Approximately 2 years old.
Growth habit: Strong, compact.
Pot size of plant described: #1, #2, #3, #5 containers.
Overall plant shape: Round, mounded.
Height: 45 cm.
Plant spread: 97 cm.
Growth rate: Good.
Plant vigor: Good.
Branching characteristics: Opposite.
Length of primary lateral branches: 37 cm.
Diameter of lateral branches: 4 mm.
Quantity of lateral branches: Over 100.
Stem:
- *Stem appearance*.—Rounded, two small ridges 180 degrees apart on stem.
- *Stem strength*.—Strong.
- *Aspect*.—0 to 90°.
- *Color*.—Yellow-Green 144B.
- *Pubescence*.—Yes, on ridges.

Internode length: Range is 4-8 cm.

FOLIAGE

Leaf:
- *Arrangement*.—Opposite.
- *Leaf shape*.—Elliptic-oblanceolate.
- *Average length*.—Approximately 6-8 cm.
- *Average width*.—Approximately 3.5 cm.
- *Apex*.—Acuminate.
- *Base*.—Cuneate-attenuate.
- *Margin*.—Serrulate.
- *Texture of top surface*.—Leathery, midrib texture.
- *Texture of bottom surface*.—Leathery, veins have texture.
- *Color*.—Young foliage upper side: Green 143B, flushed Yellow-Green N144B. Apical section N144B. Young foliage under side: Green 143C. Mature foliage upper side: Green 143B, flushed Yellow-Green N144B. Mature foliage under side: Green 143C.
- *Venation*.—Pattern: Pinnate. Color upper side: Close to Yellow-Green 145C. Color under side: Close to Yellow-Green 145C.
- *Petiole*.—Length: 2.0 mm. Diameter: 4 mm. Petiole color upper side: Close to Yellow-Green 145C. Petiole color lower side Close to Yellow-Green 145C. Petiole texture: Smooth, pubescent.

FLOWER

Natural flowering season: Spring.
Inflorescence type and habit: Umbel.
Inflorescence height: 5-15 cm.
Inflorescence width: 6-8 cm.
Quantity of flowers per inflorescence: 2-5.
Individual flowers:
- *Flower shape*.—Salverform.
- *Flower aspect*.—Mostly outward.
- *Flowering arrangement*.—Single salverform flowers, majority grouped 2-5.
- *Size*.—Diameter: 2.5 cm. Depth: 3 cm.
- *Flower other characteristics*.—Persistence: Self-cleaning. Fragrance: None.

Bud:
- *Shape*.—Obovate-spatulate.
- *Length*.—3 cm.
- *Diameter*.—1.1 cm.
- *Color*.—Red-Purple N74C with some N74B.

Petal:
- *Petal arrangement*.—Whorled, fused at opening of throat.
- *Number of petals per flower*.—5.
- *Petal shape*.—Rounded-orbicular.
- *Petal base*.—Fused at throat.
- *Margin*.—Entire.
- *Tip shape*.—Obtuse.
- *Length*.—1.0 cm.
- *Width*.—12 mm.
- *Texture*.—Upper: Soft, smooth, delicate. Lower: Soft, smooth, delicate.
- *Color*.—When opening: Upper side: Red-Purple N74D. Under side: Red-Purple N74D. Fully open: Upper side: Purple 75A. Under side: Purple 75A.
- *Flower tube*.—Length: 0.52 cm. Diameter: base: 5 mm. Color: Purple 75A.
- *Throat*.—Texture: Soft, smooth. Color: Purple 75A Mature have stripe of Yellow 5A.

Sepal:
- *Arrangement*.—Fused at base.
- *Appearance*.—Crown-like.
- *Number*.—5.
- *Shape*.—Narrowly triangular.
- *Tip*.—Acuminate.
- *Base*.—Fused.
- *Margin*.—Entire.
- *Length*.—5 cm.
- *Width*.—<1.0 mm.

*Texture, upper*.—Smooth.
*Texture, lower*.—Smooth.
*Color*.—Upper surface at maturity: N144D. Under surface at maturity: N144D.

Peduncle:
*Length*.—16 mm.
*Diameter*.—1.5 mm.
*Color*.—Mostly N144D with some Greyed Purple 185B.
*Orientation*.—Upright/outward.
*Strength*.—Good.
*Texture*.—Smooth.

Pedicel: None.

REPRODUCTIVE ORGANS

Stamens:
*Number*.—5.
*Filament length*.—21 mm.
*Filament color*.—NN155B.

Anthers:
*Shape*.—Linear.
*Length*.—7 mm.
*Color*.—Yellow-White 158C.
*Pollen color*.—Yellow-White 158C.
*Pollen amount*.—Good.

Pistil:
*Number*.—1 per flower.
*Length*.—3 cm.
*Style*.—Length: 3.6 cm. Color: Greyed-Purple 186B.

Stigma:
*Color*.—Yellow-White 158C.
*Shape*.—Globular, flat-bottomed, lobed.

OTHER CHARACTERISTICS

Seeds and fruits: Not observed to set fruit and seeds.

Disease/pest resistance: Neither resistance nor susceptibility to normal diseases and pests of *Weigela* have been observed, aside from mildew resistance.

Temperature tolerance: The new variety tolerates temperatures between −31° C. to 38° C.

Environmental stressors: Good tolerance to wind and rain.

What is claimed is:

1. A new and distinct cultivar of *Weigela hybrida* plant named 'VUKOZ047213' as herein illustrated and described.

* * * * *